United States Patent
Honkura et al.

(10) Patent No.: US 11,112,229 B2
(45) Date of Patent: Sep. 7, 2021

(54) MAGNETIC TYPE AZIMUTH/POSITION MEASUREMENT DEVICE

(71) Applicant: ASAHI INTECC CO., LTD., Seto (JP)

(72) Inventors: Yoshinobu Honkura, Chita-gun (JP); Shinpei Honkura, Chita-gun (JP)

(73) Assignee: ASAHI INTECC CO., LTD., Seto (JP)

( * ) Notice: Subject to any disclaimer, the term of this patent is extended or adjusted under 35 U.S.C. 154(b) by 134 days.

(21) Appl. No.: 16/718,192

(22) Filed: Dec. 18, 2019

(65) Prior Publication Data

US 2020/0124396 A1 Apr. 23, 2020

Related U.S. Application Data

(63) Continuation of application No. PCT/JP2018/019393, filed on May 18, 2018.

(30) Foreign Application Priority Data

Jun. 21, 2017 (JP) .............................. JP2017-121780
Sep. 7, 2017 (JP) .............................. JP2017-172549

(51) Int. Cl.
*G01B 7/00* (2006.01)
*G01R 33/02* (2006.01)
*A61B 5/06* (2006.01)

(52) U.S. Cl.
CPC ............. *G01B 7/003* (2013.01); *G01R 33/02* (2013.01); *A61B 5/062* (2013.01)

(58) Field of Classification Search
CPC ............ G01R 33/02; A61B 5/062; A61B 1/00
See application file for complete search history.

(56) References Cited

U.S. PATENT DOCUMENTS

| 5,558,091 A | 9/1996 | Acker et al. |
| 6,288,785 B1 | 9/2001 | Frantz et al. |
| 6,707,301 B2 | 3/2004 | Goto |
| 2010/0277163 A1 | 11/2010 | Nakamura et al. |

(Continued)

FOREIGN PATENT DOCUMENTS

| EP | 1174082 A1 | 1/2002 |
| EP | 2684519 A1 | 1/2014 |

(Continued)

OTHER PUBLICATIONS

Totsu, K. et al., "Magnetic sensor system for detecting position and orientation of a catheter tip," IEEJ Transactions on Sensors and Micromachines, vol. 120-E, No. 5, Jan. 2000, pp. 211-218 (See Abstract).

*Primary Examiner* — Alvaro E Fortich
(74) *Attorney, Agent, or Firm* — Xsensus LLP

(57) ABSTRACT

A magnetic type azimuth/position measurement device is disclosed, comprising: a plurality of coils driven by circuitry, the circuitry and coils configured to selectively generate a uniform magnetic field and an inclined magnetic field in a three-dimensional space; a uniaxial magnetic field sensor configured to measure a strength of a magnetic field formed by the plurality of coils driven by circuitry; and arithmetic operation circuitry configured to receive signals representative of the strength of the magnetic field from the uniaxial magnetic field sensor and calculate a position and an azimuth of the uniaxial magnetic field sensor in the three-dimensional space.

19 Claims, 7 Drawing Sheets

(56) References Cited

U.S. PATENT DOCUMENTS

| | | | | |
|---|---|---|---|---|
| 2012/0125100 A1* | 5/2012 | Araki | ................ | G01C 19/5684 |
| | | | | 73/504.12 |
| 2013/0066193 A1* | 3/2013 | Olson | .................... | A61B 5/063 |
| | | | | 600/424 |
| 2013/0172730 A1* | 7/2013 | Cohen | ...................... | A61B 6/12 |
| | | | | 600/424 |
| 2014/0296657 A1* | 10/2014 | Izmirli | ................ | A61B 6/5264 |
| | | | | 600/301 |

FOREIGN PATENT DOCUMENTS

| | | | |
|---|---|---|---|
| JP | 63-125245 | A | 5/1988 |
| JP | 63-216552 | A | 9/1988 |
| JP | 09-503410 | A | 4/1997 |
| JP | 2002-94280 | A | 3/2002 |
| JP | 2003-10147 | A | 1/2003 |
| JP | 2003-117004 | A | 4/2003 |
| JP | 2008-032815 | A | 2/2008 |
| JP | 2010-179116 | A | 8/2010 |
| JP | 4875110 | B2 | 2/2012 |
| JP | 2013-178153 | A | 9/2013 |
| JP | 2015-134166 | A | 7/2015 |
| JP | 5839527 | B1 | 1/2016 |
| WO | 94/04938 | A1 | 3/1994 |
| WO | 96/41119 | A1 | 12/1996 |
| WO | 97/00043 | A1 | 1/1997 |

\* cited by examiner

MAGNETIC TYPE AZIMUTH/POSITION MEASUREMENT DEVICE

CROSS REFERENCES TO RELATED APPLICATIONS

This application is a bypass continuation of PCT filing PCT/JP2018/019393, filed May 18, 2018, which claims priority to JP 2017-121780, filed on Jun. 21, 2017, and JP 2017-172549, filed Sep. 7, 2017, the entire contents of each are incorporated herein by reference.

TECHNICAL FIELD

The present disclosure relates to a magnetic type azimuth/position measurement device to find a position and an azimuth of a motion device with an embedded magnetic field sensor in artificially generated three-dimensional magnetic field space.

BACKGROUND

With the extensive use of high technology in the medical fields, including in vivo motion devices such as gastro cameras, catheters, and vascular endoscopes, there is growing demand for detecting a position and an azimuth of such devices. Among the methods for measuring a position and an azimuth is the use of a magnet or electromagnet embedded in a device and an external magnetic field sensor (Patent Literature 1), a system combining a uniaxial magnetic field sensor in a device, two magnetic field sensors at two predetermined positions, and an external magnetic field generating device (Patent Literature 2), and a system combining three external magnetic field generating devices and a magnetic field sensor embedded in a distal end of a guide (Patent Literature 3).

The space available for a sensor embedded in the distal end of a catheter, or similar device, is normally very small. In such applications, the available space may be on the order of 0.2 mm in diameter and 0.5 mm or smaller in length. Typically, as a magnet or a magnetic field sensor installable in such a device is reduced in size, the measurement accuracy of a position is deteriorated. Moreover, as the targeted three-dimensional space becomes larger, the measurement accuracy of a position by the magnetic field sensor is deteriorated. A conflicting relationship exists between the size of a magnetic field sensor and the size of space to be measured and the positioning accuracy. Thus, it is a difficult problem to measure a position of the distal end of a catheter with high accuracy.

Therefore, there have not been achieved the spatial resolution of 20 μm or smaller, the azimuth resolution of 0.2° or smaller, a positional error or 100 μm or smaller, and an azimuth error of 1° or smaller.

CITATION LIST

Patent Literature

Patent Literature 1: Japanese Patent Application Laid-open No. 2003-117004
Patent Literature 2: Japanese Patent Application Laid-open No. 2010-179116
Patent Literature 3: Japanese Patent Application Laid-open No. 2015-134166
Patent Literature 4: Japanese Patent No. 5839527

SUMMARY

The present application describes a magnetic type azimuth/position measurement device, comprising: a plurality of coils driven by circuitry, the circuitry and coils configured to selectively generate a uniform magnetic field and an inclined magnetic field in a three-dimensional space; a uniaxial magnetic field sensor configured to measure a strength of a magnetic field formed by the plurality of coils driven by circuitry; and arithmetic operation circuitry configured to receive signals representative of the strength of the magnetic field from the uniaxial magnetic field sensor and calculate a position and an azimuth of the uniaxial magnetic field sensor in the three-dimensional space.

DETAILED DESCRIPTION

Figure 1:
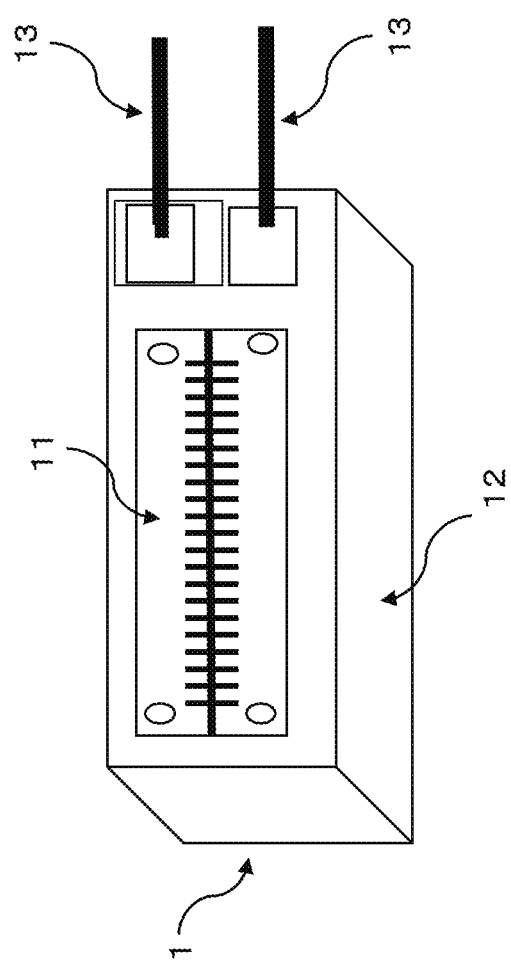
FIG. 1 illustrates a schematic view of a GSR sensor according to an embodiment.

The embodiments of the present disclosure are directed to a magnetic type azimuth/position measurement device capable of generating a three-dimensional magnetic field in space sufficient for a whole body of a patient and measuring an azimuth and a position of a motion device with an embedded magnetic field sensor, in the sufficiently large three-dimensional space, with a spatial resolution of 20 μm or smaller, an azimuth resolution of 0.2° or smaller, a positional error of 100 μm or smaller, and an azimuth error of 1° or smaller.

In embodiments of the present disclosure, a super high-sensitivity uniaxial micro magnetic sensor such as a GSR (GHz-Spin-Rotation) sensor provided at a given position in a motion device and an external magnetic field generating device capable of generating a three-dimensional uniform magnetic field and inclined magnetic field may be combined to achieve the capabilities discussed above.

In the descriptions of the various embodiments of the present disclosure, a three-dimensional space is characterized by three values that refer to measurements in different directions (coordinate axes). And while the descriptions here use the traditional orthogonal coordinate axes X, Y and Z, any three directions can be chosen, provided that vectors in these directions meet certain constraints (for example, they do not all lie in the same plane). Other representations, including cylindrical coordinates and spherical coordinates, may be used without departing from the essential spirit and scope of the present disclosure.

A three-dimensional magnetic field generating device may include a combination of three pairs of coils generating an inclined magnetic field in an X-axis, Y-axis, and Z-axis directions and three pairs of coils generating a uniform magnetic field in the X-axis, Y-axis, and Z-axis directions. Alternatively, a direction of a current applied to an inclined magnetic field generating device may be reversed to generate a uniform magnetic field. This allows omission of the uniform magnetic field coil pair generating a uniform magnetic field in such a direction. Furthermore, the coil structure of the inclined magnetic field generating coil pair and the uniform magnetic field generating coil pair may be selected appropriately.

The measurement principle of the embodiments of the present disclosure is such that the three-dimensional magnetic field generating device generates a uniform magnetic field as a reference in the order of the X-axis coil, Y-axis coil, and Z-axis coil, and a uniaxial magnetic field sensor sequentially measures the uniform magnetic fields to obtain measurement values hx, hy, hz. The direction cosines for the axes of the magnetic field sensor are hx=cos θ, hy=cos η, and hz=cos φ. Moreover, on the basis of the azimuth vector and the direction cosines, azimuth angles θ, η, φ may be calculated. On the basis of such values, the azimuth vector n (hx, hy, hz) in three-dimensional space (O-XYZ space) is determined.

Here, the X-axis coil indicates a coil pair capable of giving a uniform magnetic field in the X-axis direction.

Next, inclined magnetic fields are generated in the order of the X-axis coils, Y-axis coils, and Z-axis coils by the three-dimensional magnetic field generating device including three pairs of coils arranged in the X-axis, Y-axis, and Z-axis directions.

The X-axis coil generates an inclined magnetic field with an inclination gradient of a given ratio relative to the X, Y and Z axes. In the case of a Maxwell coil pair, when the inclination gradient of the X axis is 1, the inclination gradient of the Y axis and the Z axis is −0.5. Moreover, in the case of a parallel four wire coil pair, two X-axis coil pairs are arranged in the Y-axis direction or the Z-axis direction so that four coils form a set of coil pairs, in which four line currents flow in the Y-axis direction or the Z-axis direction. If the coils are arranged so that four line currents flow in the Y-axis direction, an inclined magnetic field occurs only in the X axis and the Z axis. Meanwhile, if the coils are arranged so that four line currents flow in the Z-axis direction, an inclined magnetic field occurs only in the X axis and the Y axis. Here, the inclination gradient of the X axis is equal to the inclination gradient of the Z axis or the Y axis.

In the embodiments of the present disclosure, the structure of the inclined magnetic field generating device is appropriately selected in accordance with an object.

The uniaxial magnetic field sensor sequentially measures the strength of such inclined magnetic fields to obtain measurement values mHx, mHy, mHz. Such measurement values are obtained by detecting inclined magnetic fields in the X-axis, Y-axis, and Z-axis directions by the uniaxial sensor. That is, with the generation of the inclined magnetic field (Hxx, Hxy, Hxz) by the X-axis coil, the inclined magnetic field (Hyx, Hyy, Hyz) by the Y-axis coil, and the inclined magnetic field (Hzx, Hzy, Hzz) by the Z-axis coil, the following set of simultaneous equations (1) is formed while considering an azimuth of the uniaxial sensor:

$$mHx = \cos\theta Hxx + \cos\eta Hxy + \cos\varphi Hxz$$

$$mHy = \cos\theta Hyx + \cos\eta Hyy + \cos\varphi Hyz$$

$$mHz = \cos\theta Hzx + \cos\eta Hzy + \cos\varphi Hzz \tag{1}$$

In the case where the parallel four wire coil is adopted only for the Z axis so that four line currents flow in the Y-axis direction, while the Maxwell coil pairs are adopted for the X axis and the Y axis, if inclined magnetic fields are sequentially generated in the X-axis coil, Y-axis coil, and Z-axis coil, in which an inclination gradient by the X-axis coil is ax, an inclination gradient by the Y-axis coil is ay, and an inclination gradient by the Z-axis coil is az, the following nine expressions are formed with a position of the magnetic field sensor R (X, Y, Z).

$$Hxx = aX,$$

$$Hxy = -0.5aY,$$

$$Hxz = -0.5aZ,$$

$$Hyx = -0.5aX,$$

$$Hyy = aY,$$

$$Hyz = -0.5aZ,$$

$$Hzx = aZ,$$

$$Hzy = 0,$$

$$Hzz = aX$$

The above-described expressions are substituted in the simultaneous equations (1), the following set of simultaneous equations (2) is formed.

$$mHx = ax(\cos\theta \cdot X - 0.5\cos\eta \cdot Y - 0.5\cos\varphi \cdot Z)$$

$$mHy = ay(-0.5\cos\theta \cdot X + \cos\eta \cdot Y - 0.5\cos\varphi \cdot Z)$$

$$mHz = az(\cos\theta \cdot Z + \cos\varphi \cdot X) \tag{2}$$

In the case where the parallel four wire coil is adopted for all of three coil pairs, if four line currents flow in the Z-axis direction in the X-axis coil, four line currents flow in the X-axis direction in the Y-axis coil, and four line currents flow in the Y-axis direction in the Z-axis coil, the following set of simultaneous equations (3) is formed.

$$mHx = ax(X\cos\eta + Y\cos\theta)$$

$$mHy = ay(Y\cos\varphi + Z\cos\eta)$$

$$mHz = az(Z\cos\theta + X\cos\varphi) \tag{3}$$

From the equations (2) and (3), the position R (X, Y, Z) of the magnetic field sensor may be calculated.

A singular point may be processed in the following manner. When any one of the direction cosines hx=cos θ, hy=cos η, hz=cos φ of the axes is zero, generated magnetic field space is rotated by a given angle with the rest of axes perpendicular to a surface formed by the axis where the direction cosine is zero and a specific axis where the direction cosine is the largest as a rotation axis. Thus, the value of the direction cosine for each axis is not zero, which removes a singular point.

For example, in the case of Hx=0, the magnetic field space is rotated by a given angle with an axis perpendicular to both the X axis and either the Y axis or the Z axis with a larger direction cosine, as a rotation axis. In a magnetic field space coordinate system after rotation, the azimuth vector n (hx, hy, hz) and the position R (X, Y, Z) are calculated. Thereafter, a position and an azimuth in the original coordinate system are calculated on the basis of the expression of coordinate rotation.

If an external magnetic field given by terrestrial magnetism, an iron machine device, a reinforced building, and the like exists, the three-dimensional magnetic field generating device cancels such external magnetic fields to keep zero magnetic field in the three-dimensional space before the start of measurement. This makes it possible to measure, with high accuracy, a direction vector coordinate position of the magnetic field sensor in the coordinate system.

To continuously perform the above-described operation for short time, it is preferable to devise the method of giving a magnetic field. For example, as the timing of applying a current to the coils of the axes, a uniform magnetic field is generated first for 5 msec for each axis and then an inclined magnetic field is generated for 5 msec for each axis. If such operation is repeated, one measurement takes 30 msec, enabling 33 times of measurement per second.

Moreover, if a pulse DC current is applied to each coil of the axes for 0.1 msec while switching the coils, one measurement takes 0.6 msec. Furthermore, it is also possible that a DC current and an AC current are overlapped and applied to the coils of the axes, and an azimuth is calculated on the basis of a value of the AC current, while an inclined magnetic field is measured on the basis of a value of the DC value. This allows calculation of a position of the sensor. Such devises only allow the calculation in the embodiments of the present disclosure to be more efficient.

The size of the coils of the three-dimensional magnetic field generating device is preferably about 50 cm to 3 m in diameter while considering the size and the region of a lesion of a patient. The size of three-dimensional space of a uniform magnetic field is about 10% of the diameter. If the diameter is 1 m, the size of three-dimensional space is about 10 cm. With a large lesion to be treated, a measurement area needs to be expanded. In such a case, the three-dimensional magnetic field generating device or a bed with a patient thereon is preferably movable by about ±5 cm along each axis.

The strength of the inclined magnetic field is preferably in the range of about 1 G to about 10 G at a position of 5 cm to 10 cm from the origin, and the gradient is preferably in the range of about 0.02 mG/1 µm to about 0.2 mG/1 µm.

As the uniaxial magnetic field sensor, there is adopted a GSR sensor in which a GSR sensor element (magnetic detection element) is integrated with an electronic circuit ASIC. The size of the GSR sensor allows embedding thereof in a motion device such as a catheter. In the case of a catheter, the GSR sensor is preferably small with a width in the range of about 0.1 mm to about 0.3 mm, a thickness in the range of about 0.05 mm to about 0.3 mm, and a length in the range of about 0.3 mm to about 1.5 mm. As the GSR sensor, only a uniaxial element is provided, which allows the length of a magnetic wire as a magneto-sensitive body to be in the range of about 0.2 mm to about 1.0 mm. With a coil pitch in the range of about 2 µm to about 5 µm, there may be adopted a magnetic field sensor with very high sensitivity improving the sensitivity from 40 mV/G to 1000 mV/G and the resolution of the magnetic field sensitivity from 0.05 mG/bit to 1 mG/bit.

Moreover, the ASIC transfers digital signals after analog-to-digital (A/D) conversion to an external arithmetic operation circuitry (processor, or the like) in which an azimuth and a position are calculated using a given program.

With the above-described GSR sensor provided at the distal end of a catheter, for example, it is possible to achieve at the same time both characteristics of the sufficient size of three-dimensional space (spherical body with a diameter of 10 cm) and the position/azimuth resolution and the accuracy (spatial resolution of 20 µm or smaller, azimuth resolution of 0.2° or smaller, positional error or 100 µm or smaller, and azimuth error of 1° or smaller).

With the combination of the three-dimensional magnetic field generating device and the uniaxial magnetic field sensor generating a uniform magnetic field and an inclined magnetic field, it is possible to calculate an in vivo position and azimuth of an in vivo motion device with high accuracy.

A magnetic type azimuth/position measurement device includes a three-dimensional magnetic field generating device that generates a uniform magnetic field and an inclined magnetic field along an X axis, a Y axis, and a Z axis in given three-dimensional space, a uniaxial magnetic field sensor that measures the strength of the magnetic field, and an arithmetic operation circuitry that calculates a position and an azimuth of the magnetic field sensor in the three-dimensional space.

In the magnetic type azimuth/position measurement device, the three-dimensional magnetic field generating device includes a parallel four wire coil for at least one of the X axis, the Y axis, and the Z axis.

In the magnetic type azimuth/position measurement device, the three-dimensional magnetic field generating device includes two types of coils of a coil forming an inclined magnetic field and a Helmholtz coil generating a uniform magnetic field.

In the magnetic type azimuth/position measurement device, a uniform magnetic field as a reference is sequentially generated in the X axis, Y axis, and Z axis using the three-dimensional magnetic field generating device, the values of the uniform magnetic fields are measured by the magnetic field sensor to calculate, on the basis of the three measurement values, an azimuth vector of the magnetic field sensor in the three-dimensional space (O-XYZ space) and direction cosines for the axes of the magnetic field sensor.

Next, the inclined magnetic field is sequentially generated in the X axis, Y axis, and Z axis while maintaining an azimuth of the magnetic field sensor in the azimuth to measure the values of the inclined magnetic fields by the magnetic field sensor at a given position, so that the given position of the magnetic field sensor is calculated on the basis of the three measurement values and the direction cosines for the axes of the magnetic field sensor.

In the azimuth/position measurement device, the magnetic field distribution strength in the three-dimensional space is measured by the magnetic field sensor with the resolution of 1 mG or smaller, and the measurement value is digitally converted and transferred to an external arithmetic operation circuitry, so that a position of the magnetic field sensor in the three-dimensional space is measured with the spatial resolution of 20 µm or smaller and calculated with the accuracy of 100 µm or smaller, and an azimuth of the magnetic field sensor in the three-dimensional space is measured with the spatial resolution of 0.2° or smaller and calculated with the accuracy of 1° or smaller.

In the magnetic type azimuth/position measurement device, the three-dimensional magnetic field generating device cancels an external magnetic field to keep zero external magnetic field in the three-dimensional space before the start of measurement.

In the magnetic type azimuth/position measurement device, when any one of direction cosines of the axes is zero, generated magnetic field space is rotated by a given angle with a remaining axis perpendicular to a surface formed by a specific axis where the direction cosine is largest and the axis where the direction cosine is zero as a rotation axis, so that a value of the direction cosine for each axis is not zero.

The following will describe embodiments of the present disclosure with reference to FIGS. 1 to 7.

FIG. 1 illustrates a schematic view of a GSR sensor 1 according an embodiment. The GSR sensor 1 may include a uniaxial GSR element 11 integrated with an ASIC 12. In some embodiments, GSR element 11 may include, on a substrate, one or more magnetic wires, a detection coil surrounding the one or more magnetic wires, and electrodes necessary for wire energization, coil voltage detection, and connection to ASIC 12.

One or more magnetic field measurement values may be converted into digital signals and transferred to external arithmetic operation circuitry (such as a processor or CPU) through two cables 13, where they may be further converted into a value of a position and an azimuth. In some embodiments, the digital signals representing the one or more magnetic field measurement values may be transmitted to external arithmetic operation circuitry via a wireless channel. In such embodiments, the two cables 13 may be replaced by an antenna structure or may be eliminated entirely.

Figure 2:
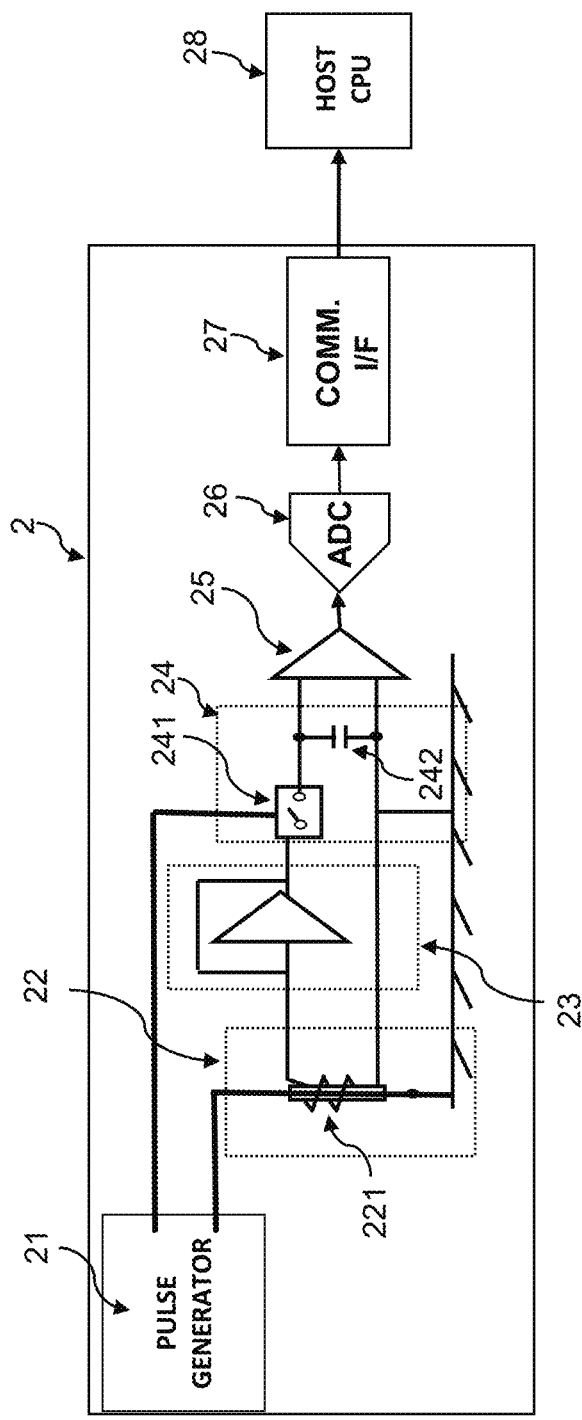
FIG. 2 illustrates an electronic circuit diagram according to an embodiment.

FIG. 2 illustrates an electronic circuit 2 according to some embodiments. In some embodiments, electronic circuit 2 may be implemented in ASIC 12 (FIG. 1). Electronic circuit 2 may include a pulse generating circuit 21 for generating a pulse current to GSR sensor 221 (GSR sensor 1 in FIG. 1), an input circuit 22 for receiving a coil voltage from GSR sensor 221 (GSR sensor 1 in FIG. 1), a pulse compliant buffer circuit 23, a sample and hold circuit 24 with an electronic switch 241 for detecting a peak voltage of an output waveform of a coil voltage and a capacitor 242 with a capacitance of about 4 pF to about 100 pF for holding a peak voltage, an amplifier 25, an A/D converter 26, and a communication interface 27. The amplifier 25 includes a programming amplifier for amplification before A/D conversion. The communication interface 27 provides for transmission of magnetic field measurement values to an external processor such as a host CPU 28.

In some embodiments, pulse generating circuit 21 in electronic circuit 2 may generate pulse current to be applied to a magnetic wire in GSR sensor 1 (FIG. 1) with a pulse frequency in the range of about 0.2 GHz to about 4 GHz. The pulse current may have the strength required to generate an over 1.5 times larger circumferential magnetic field than the magnetic anisotropy field on a surface of the magnetic wire.

In some embodiments, a coil voltage occurring at the time of pulse energization is transmitted to the sample and hold circuit 24 through pulse compliant buffer circuit 23. In some embodiments, where the number of winding of the coil in GSR sensor 1 is small, the coil voltage may be transmitted directly to the sample and hold circuit.

Figure 3:
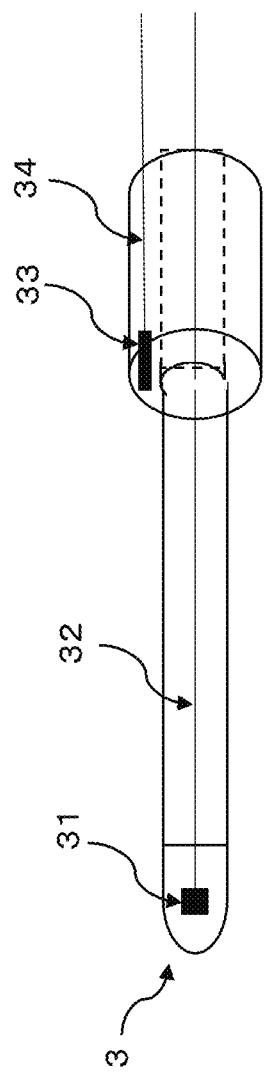
FIG. 3 illustrates a schematic view of a medical device with an embedded GSR sensor according to an embodiment.

FIG. 3 illustrates a schematic view of a medical device 3, such as a catheter, with an embedded GSR sensor, according to some embodiments. The GSR sensor 31 (GSR sensor 1 in FIG. 1), as a magnetic field sensor provided at a distal end of a medical device 3, may have a width in the range of about 0.1 mm to about 0.2 mm, a thickness in the range of about 0.05 mm to about 0.10 mm in, and a length in the range of about 0.4 mm to 1.0 mm. In some embodiments, the GSR sensor 31 may communicate with an external processor such as a host CPU 28 (FIG. 2) through cable 32. In some embodiments, the GSR sensor 31 may communicate with an external processor via a wireless channel. In such embodiments, the cable 32 may be replaced by an antenna structure or may be eliminated entirely. In some embodiments, an additional GSR sensor (long type) 33 may be enclosed in medical device 3 at a point away from the distal end for additional magnetic field measurement. GSR sensor (long type) 33 may communicate with an external processor such as a host CPU 28 (FIG. 2) through cable 34 or via a wireless channel.

In some embodiments, the GSR sensor 1 may have a sensitivity in the range of about 40 mV/G to about 1000 mV/G, a standard error of about 1 mG or smaller, and a resolution of about 16 bits with a digital precision of in the range of about 0.05 mG/bit to about 1 mG/bit.

Figure 4:
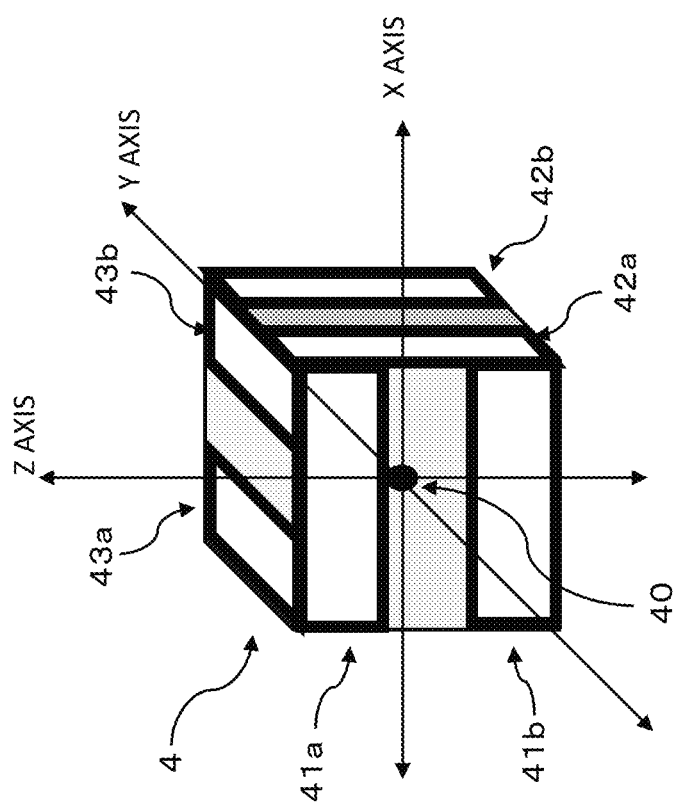
FIG. 4 illustrates a schematic view of a configuration of a three-dimensional magnetic field generating device including parallel four wire coils for three axes according to an embodiment.
Figure 5:
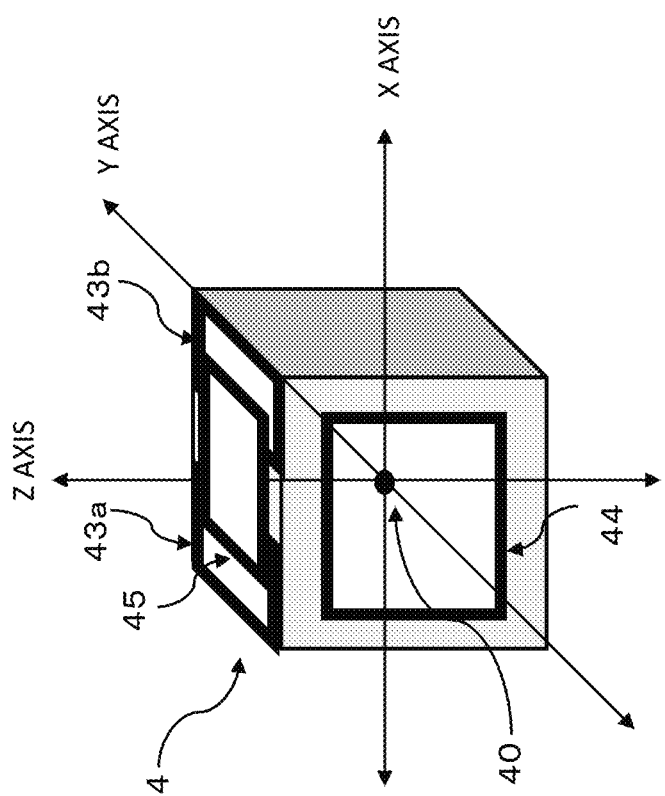
FIG. 5 illustrates a schematic view of a configuration of a three-dimensional magnetic field generating device including parallel four wire coils for one axis according to an embodiment.
Figure 6:
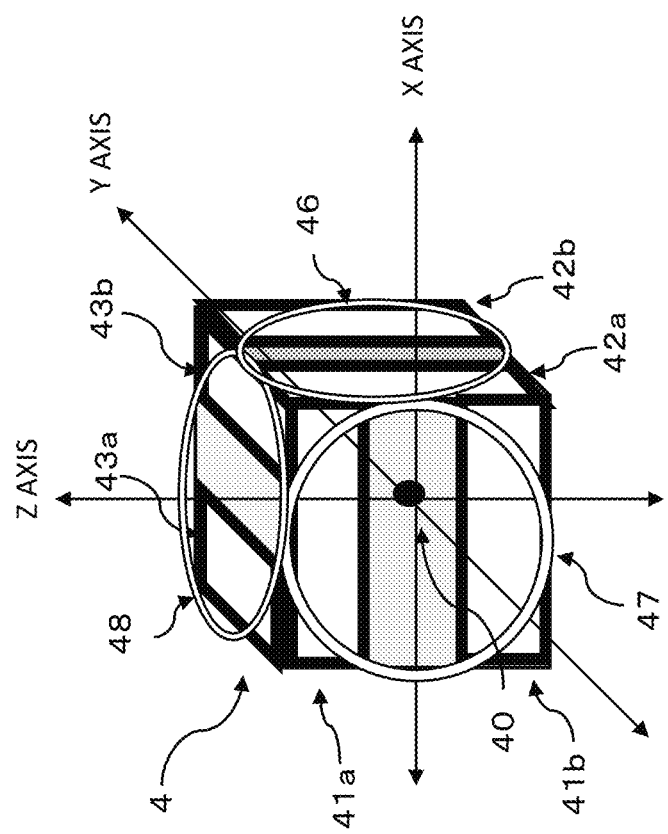
FIG. 6 illustrates a schematic view of a configuration of a three-dimensional magnetic field generating device including coils generating an inclined magnetic field and Helmholtz coils forming a uniform magnetic field according to an embodiment.

FIGS. 4 to 6 illustrate schematic views of configurations of a three-dimensional magnetic field generating device, according to some embodiments of the present disclosure. Referring to FIGS. 4 to 6, a three-dimensional magnetic field generating device 4 may include various coil pairs provided in each axial direction, and has a substantially cube form with a size in the range of about 50 cm to about 3 m per side. The size of space where a uniform magnetic field occurs is ±2.5 cm to ±15 cm with a center of the cube 40 as an origin. The strength of the inclined magnetic field may be in the range of about 1 G to about 10 G at a position of 5 cm to 10 cm from the origin, and the gradient may be in the range of about 0.05 mG/1 µm to about 1 mG/1 µm.

In some embodiments, in the three-dimensional magnetic field generating device 4, a parallel four wire coil may be provided for at least one axis, as a coil forming an inclined magnetic field. In the three-dimensional magnetic field generating device 4 illustrated in FIG. 4, a parallel four wire coil may be provided for all of three axes (X axis, Y axis, and Z axis). Two coils 41a, 41b are arranged on one surface (near-side surface in FIG. 4) of the X axis, and two coils are arranged on the other surface (far-side surface hidden in FIG. 4) thereof, so that four coils are provided in parallel. Next, two coils 42a, 42b are arranged on one surface (right-side hidden in FIG. 4) of the Y axis, and two coils are arranged on the other surface (left-side surface omitted in FIG. 4) thereof, so that four coils are provided in parallel. Then, two coils 43a, 43b are similarly arranged on one surface (upper surface) of the Z axis, and two coils are arranged on the other surface (lower surface hidden in FIG. 4) thereof, so that four coils are provided in parallel.

In the coil pair arranged on the surface (near-side surface) of the X axis, when a current is applied to the coil 41a and the coil 41b in the same direction, a uniform magnetic field in the Z-axis direction occurs. Meanwhile, when a current is applied thereto in opposite directions from each other, an inclined magnetic field with the same gradient occurs in both the Y axis and the Z axis.

Next, in the three-dimensional magnetic field generating device 4 illustrated in FIG. 5, a parallel four wire coil is arranged only for one axis (X-axis). For the other two axes, there are arranged a normal coil pair. The Y-axis coil 44 is arranged on the right-side surface and a second coil on the left-side surface (hidden), while the Z-axis coil 45 is arranged on the near-side surface and a second coil on the far-side surface (hidden).

In any coil pair, if a current is applied in the same direction, a uniform magnetic field occurs. Meanwhile, if a current is applied in opposite directions from each other, an inclined magnetic field occurs.

FIG. 6 illustrates a schematic view of a configuration of a three-dimensional magnetic field generating device, including coils generating an inclined magnetic field and Helmholtz coils generating a uniform magnetic field, according to an embodiment of the present disclosure. Device 4, as illustrated in FIG. 6, may include three sets of coil pairs of parallel four wire coils forming an inclined magnetic field (as described above with reference to FIG. 4) and three sets of Helmholtz coil pairs (46, 47, 48, along with three associated Helmholtz coils hidden in FIG. 6) forming a uniform magnetic field. With independent coils for generating a uniform magnetic field, it may be possible to improve the accuracy of a uniform magnetic field and improve the azimuth accuracy of a uniaxial magnetic sensor and thus improve the positioning accuracy of the sensor.

Figure 7:
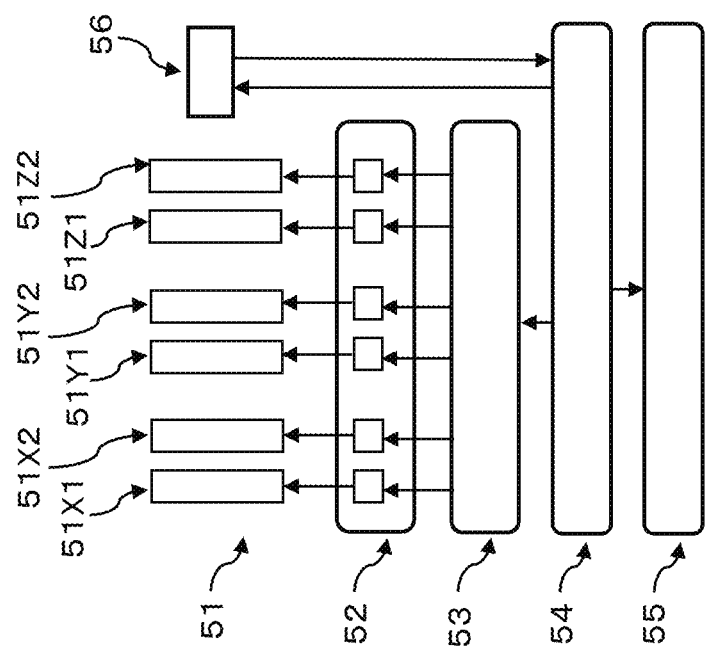
FIG. 7 illustrates a conceptual block diagram illustrating a magnetic type azimuth/position measurement device according to an embodiment.

FIG. 7 illustrates a conceptual block diagram of the magnetic type azimuth/position measurement device and measurement method, according to an embodiment.

Referring to FIG. 7, the azimuth/position measurement device may include coils 51, a power source 52, a control device 53, arithmetic operation circuitry (Host CPU) 54, a display device 55, and a GSR sensor 56.

In some embodiments, during operation, a three-dimensional uniform magnetic field may be generated while a current applied to the coils 51X1, 51Y1, 51Z1 is switched sequentially by the power source 52 under the control of the control device 53. Next, an inclined magnetic field may be generated while a current applied to the coils 51X2, 51Y2, 51Z2 is switched sequentially by the power source 52 under the control of the control device 53. The GSR sensor 56 may be used to measure the magnetic fields, transfer the result to the arithmetic operation circuitry 54 to calculate an azimuth and a position of the sensor as a measurement value.

The azimuth may be measured by sequentially generating the uniform magnetic field using coils 51X1, 51Y1, 51Z1, sequentially measuring the uniform magnetic field as a reference in the X-axis, Y-axis, and Z-axis directions using the GSR sensor 56 (uniaxial magnetic field sensor), and performing calculations using the measurement values hx, hy, hz and direction cosines for the axes of the magnetic field sensor $hx=\cos\theta$, $hy=\cos\eta$, $hz=\cos\varphi$. The azimuth angles $\theta$, $\eta$, $\varphi$ may be calculated on the basis of the azimuth vector and the direction cosines. On the basis of such values, the azimuth vector n (hx, hy, hz) in three-dimensional space (O-XYZ space) may be determined.

Next, the position may be calculated by measuring the inclined magnetic fields generated in the X-axis, Y-axis, and Z-axis coils (51X2, 51Y2, 51Z2) using the GSR sensor 56, and performing calculations using the measurement values mHx, mHy, mHz and the measured direction cosines using the set of simultaneous equations (1) above.

In the case where the parallel four wire coil is adopted only for the Z axis so that four line currents flow in the Y-axis direction, and Maxwell coil pairs are adopted for the rest of axes, the position may be calculated using the set of simultaneous equations (2) above.

In the case where the parallel four wire coils are adopted for all of three pairs of coils (as in FIGS. 4 and 6), if four line currents are applied in the Z-axis direction in the X-axis coil, four line currents are applied in the X-axis direction in the Y-axis coil, and four line currents are applied in the Y-axis direction in the Z-axis coil, the position may be determined using the set of simultaneous equations (3) above.

As the timing of sequentially applying a current to the coils in the X axis, Y axis, and Z axis to measure an azimuth and a position, a uniform magnetic field may be generated first for approximately 5 ms for each axis and then an inclined magnetic field may be generated for 5 ms for each axis. If such an operation is repeated, one measurement takes approximately 30 ms, enabling a measurement rate of approximately 33 measurements per second.

In some embodiments, to achieve measurement at a higher speed, a pulse DC current with a width in the range of about 0.1 ms to about 0.3 ms may be applied in the same direction to generate a uniform magnetic field, and then a current may be applied in the opposite directions from each other to generate an inclined magnetic field. This operation may be repeated with the interval in the range of about 0.6 ms to about 1.8 ms, enabling 560 to 1600 times of measurement per second. enabling a measurement rate in the range of about 560 to about 1600 measurements per second.

In some embodiments, a singular point may be processed in the following manner. When any one of the direction cosines $hx=\cos\theta$, $hy=\cos\eta$, $hz=\cos\varphi$ of the axes is zero, the magnetic field space may be rotated by a given angle with the remaining axis perpendicular to a surface formed by the axis where the direction cosine is zero and a specific axis where the direction cosine is the largest as a rotation axis. Thus, the value of the direction cosine for each axis is not zero, which removes a singular point.

For example, in the case of Hx=0, the magnetic field may be rotated by about 15° to 30° with an axis perpendicular to both the X axis and either the Y axis or the Z axis with a larger direction cosine as a rotation axis. In a magnetic field space coordinate system after rotation, the azimuth vector n (hx, hy, hz) and the position R (X, Y, Z) may be calculated. Thereafter, a position and an azimuth in the original coordinate system are calculated on the basis of the expression of coordinate rotation.

In some embodiments, when an external magnetic field in the range of about 0.5 G to about 2 G caused by, for example, terrestrial magnetism, an iron machine device, a reinforced building, and the like exists, the three-dimensional magnetic field generating device may cancel such an external magnetic field to keep a 0 G magnetic field in the three-dimensional measurement space before the start of measurement. This makes it possible to measure, with high accuracy, a direction vector coordinate position of the magnetic field sensor in the coordinate system.

In an embodiment, the magnetic field distribution strength in three-dimensional space may be measured with a resolution of about 1 mG (100 nT) or smaller, and the position of the magnetic field sensor in the three-dimensional space may be measured with an accuracy of about 50 μm or smaller. In addition, the azimuth of the three-dimensional space may be measured with an accuracy of 1° or smaller.

In other words, in the space of ±5 cm to ±10 cm with the origin of the cube-form three dimensional magnetic field generating device as a center, it is possible to achieve the azimuth resolution of 0.05° to 0.2°, an azimuth error of 0.2° to 1°, the positional resolution of 0.4 μm to 20 μm, and a positional error of 20 μm to 50 μm or smaller.

EXAMPLE

Referring to FIGS. 1-3, in an example embodiment, the size of the GSR sensor 1 (31 in FIG. 3) provided at a distal end of the catheter 3 is 0.15 mm in width, 0.07 mm in thickness, and 0.5 mm in length. The GSR sensor 1 includes the uniaxial GSR element 11 integrated with the ASIC 12. The measurement value is converted into digital signals, transferred to an external arithmetic operation circuitry through two cables 13 (or, in an alternative embodiment, through a wireless channel), and converted into a value of a position and an azimuth.

In an example embodiment, the GSR sensor 1 has a sensitivity of about 500 mV/G, with a standard deviation σ of 0.1 mG, and a resolution of 16 bits with magnetic sensitivity of 0.1 mG/bit.

In an example embodiment, the electronic circuit 2 (FIG. 2) generates a pulse current applied to the magnetic wire with a pulse frequency of about 1.3 GHz. The pulse current has the strength required to generate an over 1.5 times larger circumferential magnetic field than the magnetic anisotropy field on a surface of the magnetic wire.

In an example embodiment, the coil voltage occurring at the time of pulse energization is transmitted to a sample and hold circuit 24 through a pulse-support buffer circuit 23.

In an example embodiment, the three-dimensional magnetic field generating device 4 has the structure illustrated in FIG. 6, and the size of the cube form is about 1.5 m per side. The size of space where a uniform magnetic field occurs is ±10 cm with a center of the cube 40 as a center. The strength of the inclined magnetic field is about 2 G at a position of 10 cm from the origin, and the gradient is about 0.2 mG/1 μm.

In an example embodiment, a power source is attached to each of six coils for generating a uniform magnetic field and an inclined magnetic field. A DC current with a width of 5 ms is sequentially applied in the same direction in the X axis, Y axis, and Z axis to generate a uniform magnetic field, and then a current is applied in opposite directions to generate an inclined magnetic field. The measurement is repeated with the interval of 30 ms, enabling a measurement rate of about 33 times per second.

In an example embodiment, the three-dimensional magnetic field generating device generates a uniform magnetic field as a reference in the order of the X axis, Y axis, and Z axis, and the GSR sensor 1 (uniaxial magnetic field sensor) sequentially measures the magnetic fields to obtain measurement values hx, hy, hz. The azimuth vector n (hx, hy, hz) is determined on the basis of such values. Here, with hx=cos θ, hy=cos η, hz=cos φ, the azimuth angles θ, η, φ are calculated.

Next, the position is calculated by measuring the inclined magnetic fields generated in the X-axis, Y-axis, and Z-axis coils using the uniaxial magnetic field sensor, and performing calculation using the measurement values mHx, mHy, mHz and the measured direction cosines in the following simultaneous equation:

$$mHx = ax(X \cdot \cos \eta + Y \cdot \cos \theta)$$

$$mHy = ay(Y \cdot \cos \varphi + Z \cdot \cos \eta)$$

$$mHz = az(Z \cdot \cos \theta + X \cdot \cos \varphi)$$

In an example embodiment, a singular point is processed in the following manner. When any one of direction cosines hx=cos θ, hy=cos η, hz=cos φ of the axes is zero, the generated magnetic field space is rotated by a given angle with the remaining axis perpendicular to a surface formed by the axis where the direction cosine is zero and a specific axis where the direction cosine is the largest as a rotation axis. Thus, the value of the direction cosine for each axis is not zero, which removes a singular point.

For example, in the case of Hx=0, the magnetic field is rotated by about 15° to 30° with an axis perpendicular to both the X axis and either the Y axis or the Z axis with a larger direction cosine as a rotation axis. In the magnetic field space coordinate system after rotation, the azimuth vector n (hx, hy, hz) and the position R (X, Y, Z) are calculated. Thereafter, a position and an azimuth in the original coordinate system are calculated on the basis of the expression of coordinate rotation.

In an example embodiment, when an external magnetic field in the range of about 0.5 G to about 2 G caused by, for example, terrestrial magnetism, an iron machine device, a reinforced building, and the like exists, the three-dimensional magnetic field generating device may cancel such an external magnetic field to keep a 0 G magnetic field in the three-dimensional measurement space before the start of measurement. This makes it possible to measure, with high accuracy, a direction vector coordinate position of the magnetic field sensor in the coordinate system.

In an example embodiment, in the space of ±7.5 cm with the origin 40 of the cube-form three dimensional magnetic field generating device as a center, it is possible to achieve the azimuth resolution of 0.2°, an azimuth error of 1°, the positional resolution of 10 μm, and a positional error of 50 μm or smaller.

INDUSTRIAL APPLICABILITY

The embodiments of the present disclosure enable in vivo azimuth/position measurement of an in vivo motion device such as a catheter and a vascular endoscope. The embodiments are expected to enable robotic medical treatment for advanced therapy and contribute to the widespread use thereof.

REFERENCE SIGNS LIST

1 GSR sensor
11 GSR element
12 ASIC
13 cable
2 electronic circuit
21 pulse generator
22 signal processing circuit
221 GSR element
23 buffer circuit
24 sample hold circuit
241 electronic switch
242 capacitor
25 amplifier
26 AD converter
27 communication means
28 Host CPU (arithmetic operation circuitry)
3 catheter
31 GSR sensor
32 cable
33 GSR sensor (long type)
34 cable
4 structure of three-dimensional magnetic field generating device
40 origin
41 Z-axis coil near side (Z-axis uniform magnetic field and inclined magnetic field)
42 Y-axis coil right side (Y-axis uniform magnetic field and inclined magnetic field)
43 X-axis coil upper side (X-axis uniform magnetic field and inclined magnetic field)
44 Y-axis coil (both Y-axis uniform magnetic field and inclined magnetic field)
45 Z-axis coil (both Z-axis uniform magnetic field and inclined magnetic field)

46 Helmholtz coil
47 Helmholtz coil
48 Helmholtz coil
5 configuration of three-dimensional magnetic field generating device
51 coil
51X1 X-axis uniform magnetic field coil
51X2 X-axis inclined magnetic field coil
51Y1 Y-axis uniform magnetic field coil
51Y2 Y-axis inclined magnetic field coil
51Z1 Z-axis uniform magnetic field coil
51Z2 Z-axis inclined magnetic field coil
52 power source
53 control device
54 arithmetic operation circuitry (Host CPU)
55 display device
56 GSR sensor

The invention claimed is:

1. A magnetic type azimuth/position measurement device, comprising:
  a plurality of coils driven by circuitry, the circuitry and coils configured to selectively generate a uniform magnetic field and an inclined magnetic field in a three-dimensional space;
  a uniaxial magnetic field sensor configured to measure a strength of a magnetic field formed by the plurality of coils driven by circuitry; and
  arithmetic operation circuitry configured to receive signals representative of the strength of the magnetic field from the uniaxial magnetic field sensor and calculate a position and an azimuth of the uniaxial magnetic field sensor in the three-dimensional space.

2. The magnetic type azimuth/position measurement device according to claim 1, wherein the circuitry and coils are further configured to:
  generate the uniform magnetic field sequentially in each of three orthogonal directions and wherein, for each direction, values of the uniform magnetic fields are measured by the uniaxial magnetic field sensor and wherein the arithmetic operation circuitry is further configured to calculate an azimuth vector of the uniaxial magnetic field sensor in the three-dimensional space and direction cosines for the three orthogonal directions of the uniaxial magnetic field sensor using received signals representative of a strength of the uniform magnetic field in each of the three orthogonal directions;
  generate the inclined magnetic field sequentially in each of the three orthogonal directions and wherein, for each direction, values of the inclined magnetic fields are measured by the uniaxial magnetic field sensor and wherein the arithmetic operation circuitry is further configured to calculate the position of the uniaxial magnetic field sensor using received signals representative of a strength of the inclined magnetic field in each of the three orthogonal directions and the direction cosines for the three orthogonal directions of the uniaxial magnetic field sensor.

3. The magnetic type azimuth/position measurement device according to claim 1,
  wherein the circuitry and coils are further configured to cancel an external magnetic field to maintain a zero magnetic field in the three-dimensional space before a start of measurement.

4. The magnetic type azimuth/position measurement device according to claim 1, wherein the plurality of coils includes three sets of coil pairs of parallel four wire coils forming an inclined magnetic field and three sets of Helmholtz coil pairs forming a uniform magnetic field.

5. The magnetic type azimuth/position measurement device according to claim 2, wherein
  when any one of direction cosines for the three orthogonal directions is zero, a generated magnetic field space is rotated by a predetermined angle with a remaining direction perpendicular to a surface formed by a specific direction where the direction cosine is largest and the direction where the direction cosine is zero as a rotation axis, so that a value of the direction cosine for each direction is not zero.

6. The magnetic type azimuth/position measurement device according to claim 1, wherein
  if in the inclined magnetic field generated by the three-dimensional magnetic field generating device, the strength at a position deviating from a center line of each axis deviates slightly from a position of the axis, a deviation amount is measured preliminarily to perform position calculation with high accuracy using a value of the deviation amount as a correction value.

7. The magnetic type azimuth/position measurement device according to claim 1, wherein
  the uniaxial magnetic field sensor is a GSR (GHz-Spin-Rotation) sensor.

8. The magnetic type azimuth/position measurement device according to claim 1, wherein
  the uniaxial magnetic field sensor includes a magnetic detection element with one or more magnetic wires, a detection coil surrounding the one or more magnetic wires and a signal processing circuit configured to convert a detected coil voltage into a signal representing a magnetic field strength, and has performance of measuring the magnetic field with a standard error of 1 mG or smaller.

9. A magnetic type azimuth/position measurement device, comprising:
  a plurality of coils driven by circuitry, the circuitry and coils configured to sequentially generate a uniform magnetic field and an inclined magnetic field along an X axis, a Y axis, and a Z axis in a three-dimensional space;
  a uniaxial magnetic field sensor configured to measure a strength of the uniform magnetic field and the inclined magnetic field; and
  arithmetic operation circuitry configured to calculate an azimuth vector of the uniaxial magnetic field sensor in the three-dimensional space, direction cosines for the X axis, the Y axis, and the Z axis and position of the uniaxial magnetic field sensor using signals received from the uniaxial magnetic field sensor that represent a strength of the uniform magnetic field and the inclined magnetic field in each of the X axis, the Y axis, and the Z axis.

10. The magnetic type azimuth/position measurement device according to claim 9,
  wherein the circuitry and coils are further configured to cancel an external magnetic field to maintain a zero magnetic field in the three-dimensional space before a start of measurement.

11. The magnetic type azimuth/position measurement device according to claim 9, wherein
  when any one of direction cosines for the X axis, the Y axis, or the Z axis is zero, a generated magnetic field space is rotated by a predetermined angle with a remaining axis perpendicular to a surface formed by a specific axis where the direction cosine is largest and the axis where the direction cosine is zero as a rotation axis, so that a value of the direction cosine for each axis is not zero.

12. The magnetic type azimuth/position measurement device according to claim 9, wherein
the uniaxial magnetic field sensor is a GSR (GHz-Spin-Rotation) sensor.

13. The magnetic type azimuth/position measurement device according to claim 9, wherein
the uniaxial magnetic field sensor includes a magnetic detection element with one or more magnetic wires, a detection coil surrounding the one or more magnetic wires and a signal processing circuit configured to convert a detected coil voltage into a signal representing a magnetic field strength.

14. The magnetic type azimuth/position measurement device according to claim 9, wherein
the plurality of coils includes a parallel four wire coil for at least one of the X axis, the Y axis, and the Z axis.

15. The magnetic type azimuth/position measurement device according to claim 9, wherein
the plurality of coils includes two types of coils of a coil forming an inclined magnetic field and a Helmholtz coil generating a uniform magnetic field.

16. A method, using circuitry, of measuring azimuth and position comprising:
selectively generating, by the circuitry and a plurality of coils driven by the circuitry, a uniform magnetic field and an inclined magnetic field in a three-dimensional space;
measuring, by a uniaxial magnetic field sensor, a strength of a magnetic field formed by the plurality of coils driven by the circuitry at a location of the uniaxial magnetic field sensor;
receiving from the uniaxial magnetic field sensor, by the circuitry, signals representative of the strength of the magnetic field; and
calculating, by the circuitry, a position and an azimuth of the uniaxial magnetic field sensor in the three-dimensional space.

17. The method of claim 16, wherein:
the selectively generating step further comprises generating, by the circuitry, the uniform magnetic field and the inclined magnetic field sequentially in each of three orthogonal directions;
the measuring step further comprises measuring for each direction, by the uniaxial magnetic field sensor, values of the uniform magnetic field and the inclined magnetic field; and
the calculating step further comprises calculating, by the circuitry, an azimuth vector of the uniaxial magnetic field sensor in the three-dimensional space, direction cosines for the three orthogonal directions of the uniaxial magnetic field sensor and the position of the uniaxial magnetic field sensor.

18. The method of claim 16, wherein:
when any one of direction cosines, calculated in the calculating step, for the three orthogonal directions is zero, rotating a generated magnetic field space by a predetermined angle with a remaining direction perpendicular to a surface formed by a specific direction where the direction cosine is largest and the direction where the direction cosine is zero as a rotation axis, so that a value of the direction cosine for each direction is not zero.

19. The method of claim 16, further comprising:
cancelling an external magnetic field to keep zero external magnetic field in the three-dimensional space before a start of measurement.

* * * * *